United States Patent
Brown

(10) Patent No.: US 9,167,967 B2
(45) Date of Patent: Oct. 27, 2015

(54) HOME HEALTH DIGITAL VIDEO RECORDING SYSTEM FOR REMOTE HEALTH MANAGEMENT

(75) Inventor: Stephen J. Brown, Woodside, CA (US)

(73) Assignee: Robert Bosch Healthcare Systems, Inc., Palo Alto, CA (US)

( * ) Notice: Subject to any disclaimer, the term of this patent is extended or adjusted under 35 U.S.C. 154(b) by 1332 days.

(21) Appl. No.: 12/117,175

(22) Filed: May 8, 2008
(Under 37 CFR 1.47)

(65) Prior Publication Data

US 2009/0281392 A1    Nov. 12, 2009

(51) Int. Cl.
*A61B 5/00* (2006.01)
*G06Q 10/00* (2012.01)
*G06F 19/00* (2011.01)
*G06Q 50/22* (2012.01)

(52) U.S. Cl.
CPC .......... *A61B 5/0002* (2013.01); *G06F 19/3418* (2013.01); *G06Q 50/22* (2013.01); *G06F 19/363* (2013.01)

(58) Field of Classification Search
CPC ................ G06F 19/00–19/36; G06F 19/3418; G06F 19/3406; G06F 19/324; G06F 19/3456; G06F 19/327; G06F 19/363; G06F 19/322; G06F 19/345; G06F 19/3462; G06Q 50/122; G06Q 50/22–50/24; G06Q 30/00–30/04; G06Q 10/02; G06Q 10/025; G06Q 30/0601; G09B 23/00–23/40; G09B 5/00–5/08; G09B 7/00; G09B 9/00; G09B 19/00; G09B 5/065; A61B 5/0002
See application file for complete search history.

(56) References Cited

U.S. PATENT DOCUMENTS

| | | | |
|---|---|---|---|
| 5,544,649 A | 8/1996 | David et al. | |
| 6,648,820 B1 | 11/2003 | Sarel | |
| 6,936,007 B2 | 8/2005 | Quy | |
| 6,991,586 B2 * | 1/2006 | Lapcevic | 482/8 |
| 7,077,806 B2 * | 7/2006 | Ackermann et al. | 600/300 |
| 8,353,827 B2 * | 1/2013 | Brown | 600/300 |
| 8,583,030 B2 * | 11/2013 | Rao | 455/3.04 |
| 8,644,754 B2 * | 2/2014 | Brown | 434/350 |
| 2002/0082865 A1 * | 6/2002 | Bianco et al. | 705/2 |
| 2002/0186243 A1 * | 12/2002 | Ellis et al. | 345/753 |
| 2002/0188477 A1 * | 12/2002 | Ackermann et al. | 705/3 |
| 2003/0028399 A1 * | 2/2003 | Davis et al. | 705/2 |
| 2003/0229514 A2 | 12/2003 | Brown | |
| 2004/0059599 A1 | 3/2004 | McIvor | |
| 2004/0127336 A1 * | 7/2004 | Lapcevic | 482/8 |
| 2004/0219500 A1 * | 11/2004 | Brown et al. | 434/307 R |
| 2005/0283384 A1 * | 12/2005 | Hunkeler et al. | 705/2 |
| 2005/0283385 A1 * | 12/2005 | Hunkeler et al. | 705/2 |

(Continued)

*Primary Examiner* — William Thomson
*Assistant Examiner* — Shirley Jian
(74) *Attorney, Agent, or Firm* — Rahman LLC

(57) ABSTRACT

Remote health monitoring of at least one individual using at least one remote apparatus that receives and records health-related video content being delivered from a plurality of video sources. The remote apparatus also receives and stores vital sign data of an individual. Also, a user interface capable of executing a rule script having a plurality of response choices is provided in the remote apparatus. A remote server is provided that is communicatively coupled to the remote apparatus and includes a script generator for generating the rule script that is based on the vital sign data and various responses received from the individual. The various responses received from the individual are analyzed within the remote server to determine appropriate video content that can be recorded in the remote apparatus for imparting better health knowledge to the individual and monitoring their health condition accordingly.

25 Claims, 4 Drawing Sheets

(56) References Cited

U.S. PATENT DOCUMENTS

2006/0178914 A1     8/2006  Brown
2007/0156457 A1*    7/2007  Brown .............................. 705/2
2007/0299694 A1*   12/2007  Merck .............................. 705/3
2008/0004904 A1*    1/2008  Tran ................................. 705/2
2008/0268413 A1*   10/2008  Leichner ....................... 434/262
2010/0106519 A1*    4/2010  Lemke et al. ..................... 705/2
2010/0137693 A1*    6/2010  Porras et al. .................. 600/301

* cited by examiner

HOME HEALTH DIGITAL VIDEO RECORDING SYSTEM FOR REMOTE HEALTH MANAGEMENT

BACKGROUND

1. Technical Field

The embodiments herein relate generally to health management of individuals and, more particularly to, a health management system that provides health monitoring and imparts health-related knowledge to individuals.

2. Description of the Related Art

Health management of individuals and patients is now no longer confined to physicians' clinics or hospitals. With the use of the Internet and wireless technology, health conditions of individuals and patients may be monitored and controlled remotely. A typical health management system of today's age involves healthcare providers, who arrange various remote therapeutic programs for monitoring and controlling a patient's ill health conditions.

Various patients may have a wide variety of medical needs. Based on these needs the healthcare providers need to suggest appropriate therapy to the patients for achieving a cure or maintaining patient's condition at a controlled level. For example, a patient suffering from diabetes may need to be guided through a diabetes care regimen for maintaining his/her blood glucose level. Since diet, exercise, and medication all have major effects on a patient's blood glucose levels, information regarding the blood glucose level and other important health parameters such as blood pressure and weight of the diabetics should be recorded along with the timestamp information (i.e., date and time) of the recording. This information may be then forwarded to the healthcare providers of that diabetic care regimen and based on the recorded information, the care provider may suggest necessary actions to the patients. This helps a person with diabetes to closely monitor and manage hisser condition.

Such a health management system is described in U.S. Pat. No. 5,544,649, the complete disclosure of which, in its entirety, is herein incorporated by reference, and which describes an ambulatory (in the home) patient health monitoring system wherein the patient is monitored by a healthcare worker at a central station, while the patient is at a remote location. The patient may be a person having a specific medical condition being monitored or may be an elderly person desiring general medical surveillance in the home environment. Cameras are provided at the patient's remote location and at the central station such that the patient and the healthcare worker are in interactive visual and audio communication. A communications network such as an interactive cable television is used for this purpose. Various medical condition sensing and monitoring equipment are placed in the patient's home, depending on the particular medical needs of the patient. The patient's medical condition is measured or sensed in the home and the resulting data is transmitted to the central station for analysis and display. The healthcare worker then is placed into interactive visual communication with the patient concerning the patient's general well being, as well as the patient's medical condition. Thus, the healthcare worker can make "home visits" electronically, twenty-four hours a day.

Although U.S. Pat. No. 5,544,649 patent describes monitoring of patients' health at their respective homes, it and other systems like it are generally lacking as it relates to educating patients in a personalized manner in order to empower patients to do more for themselves. Interactive video communications also tend to rely on the patient and care provider to schedule a video visit and thus need to coordinate their schedules to be on the line at the same time. The problem is the shortage of healthcare providers who can deliver personalized education and care even when telehealth systems are in place.

Other home health management systems that seek to educate and monitor patients at home generally have limited ability to store and serve appropriate content to meet the wide range of individualized needs that exist in the patient population served, providing content that is general or one-size-fits-all. When such content is personalized, it is generally limited to text messaging and is rich multimedia content which is far to expensive and difficult to personalize using currently available methods.

Certain disease management programs send patients videos and educational materials via mail and follow-up by telephone to ascertain and confirm comprehension. However, such disease management programs are imprecise in their responsiveness to patient needs. Further, certain web sites also exist with a wide variety of patient educational content, however these web sites are typically not well adapted to give patients convenient and appropriate television quality video content in their own homes. In view of the foregoing, an improved remote-monitoring system for educating or imparting knowledge to patients with respect to their diseases, is needed.

SUMMARY

The embodiments herein provide a system, apparatus, and method for remote health management that facilitates recording of appropriate health-related video content at the user end. In one embodiment a plurality of distributed remote apparatuses are provided that may be programmed to receive and record health-related broadcast or cable delivered video data.

In the embodiments herein, each remote apparatus may receive the health-related video data from a plurality of video program sources wherein each source may have a plurality of channels that deliver different kinds of video programs. The health-related video data may be broadcast through satellite or delivered through cables according to the program schedules set by the respective video program sources. Each remote apparatus may be programmed to record appropriate video programs depending upon the patient's requirements.

As per the embodiments herein, each remote apparatus may have means to receive and store vital sign data of an individual or patient. The receiving means such as a sensor port may be coupled to a plurality of sensors to gather health-related data such as blood pressure, pulse rate, blood glucose level, and other health parameters. Such health information may be forwarded to a remote server where it may be used by healthcare providers for monitoring the patients and maintaining their health profiles. The health information may be further used as input variables to a set of rules to generate a rule script within a remote server. The rule script may be personalized by the healthcare providers based on the patient's profile and health condition.

This rule script may be authored by healthcare providers in the form of health-related messages and survey questions having a plurality of response choices. Each remote apparatus may also have a user interface, capable of executing the rule script. The rule script may further use as input variables, the vital sign data and various responses received from the individuals. The rule script may also contain questions relating to the health-related video content being recorded in the remote apparatus to determine if the patient has viewed the content. The responses and information collected from the plurality of remote apparatuses may further be analyzed within the remote server to determine whether the patients have comprehended the health-related video content.

In the embodiments herein, the remote apparatus may be programmed to automatically select and record appropriate health-related video content being received from the video program sources over broadcast stream or through data cables. The automatic selection and recording of the appropriate video content depends upon the individual's health requirement and profiles.

In the embodiments herein, the individuals or patients may also be allowed to select an appropriate video content being received from the video program sources over broadcast stream or data cables and record the video content in their remote apparatuses.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF THE PREFERRED EMBODIMENTS

Figure 1:
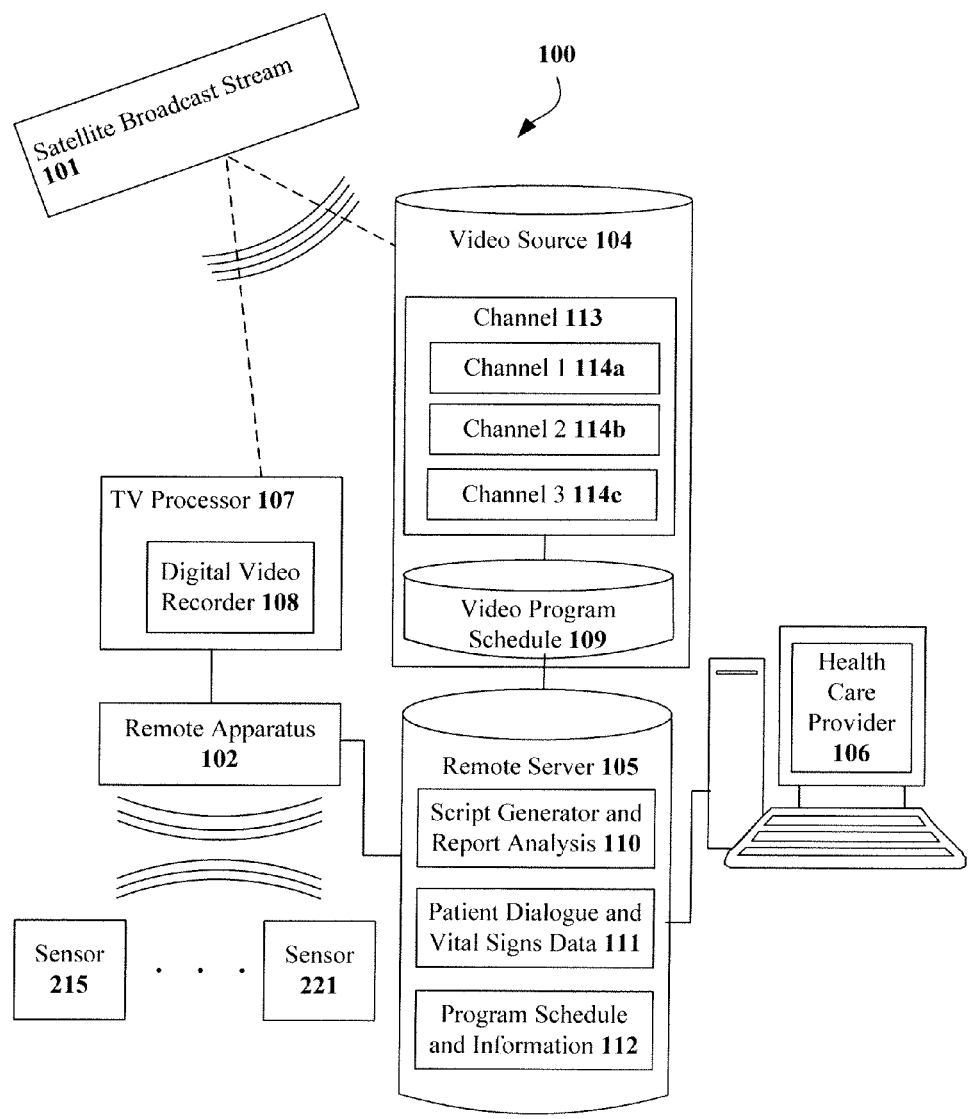
FIG. 1 is a block diagram illustrating a remote health management system according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein However, it will be apparent that one skilled in the art will recognize that embodiments herein, some of which are described below, may be incorporated into a number of different computing systems and devices. The embodiments herein may be present in hardware, software or firmware. Furthermore, connections between components within the figures are not intended to be limited to direct connections. Rather, data between these components may be modified, re-formatted, or otherwise changed by intermediary components.

Reference in the specification to "one embodiment", "in one embodiment" or "an embodiment" etc. means that a particular feature, structure, characteristic, or function described in connection with the embodiment is included in at least one embodiment herein. The appearances of the phrase "in one embodiment" in various places in the specification are not necessarily all referring to the same embodiment.

As mentioned, there remains a need for an improved remote-monitoring system for educating or imparting knowledge to patients with respect to their diseases. The embodiments herein achieve this by providing a system, apparatus, and method for remotely monitoring health of at least one individual. In one embodiment at least one remote apparatus is provided that receives and records video content being delivered from a plurality of video sources. The remote apparatus also receives and stores vital sign data of an individual. Also, a user interface capable of executing a rule script having a plurality of response choices is provided in the remote apparatus. A remote server is provided that is communicatively coupled to the remote apparatus and includes a script generator for generating the rule script based on the vital sign data and various responses received from the individual. Individuals receiving the rule script, send their response to the remote server. The various responses received from the individuals are analyzed within the remote server to determine appropriate video content that can be recorded in the remote apparatus. Referring now to the drawings and more particularly to FIGS. 1 through 4, where similar reference characters denote corresponding features consistently throughout the figures, there are shown preferred embodiments.

FIG. 1 illustrates a general block diagram of a health management system 100 according to one embodiment herein. The system 100 facilitates patient monitoring and health education by allowing the users to record selected health-related video content according to their needs and preferences.

The system 100 may include at least one programmable remote apparatus 102 for collecting patient health information and conveying the same to healthcare providers 106 via a remote server 105. The healthcare providers 106 may provide various health management programs for different individuals and patients. In one embodiment herein, the remote apparatus 102 may be connected to a television (TV) processor 107 having a digital video recorder (DVR) 108. In another embodiment, a television processor unit (not shown) may be provided wherein the television processor unit may include the television processor 107, the remote apparatus 102, and the digital video recorder 108. The remote apparatus 102 may be programmed to automatically select and record appropriate health-related video content being received by the television processor 107 from a satellite broadcast stream 101. The satellite broadcast stream 101 may broadcast a plurality of the video broadcast data all the time as per video program schedule database 109 of video program source 104. The remote server 105 may read the video program schedule 109 information and select the correct content from this stream that is most relevant to the patient's or individual's health condition. This health-related video content may then be integrated with the patient's health management program to enable the patient to view the content appropriate for his/her current health status. Further, information on whether the patient has viewed the video content and whether the patient has comprehended the educational video content may also be sent to the remote server 105 for report generation. The healthcare providers 106 may then access this information and receive the patient report from the remote server 105 for analysis and treatment.

The remote server 105 may be communicatively coupled to each remote apparatus 102 via communication links including the Internet and cable links. The health information or vital sign data may be collected through a plurality of different health sensors 215-221 coupled to each remote apparatus 102. These sensors 215-221 may provide different vital sign data of a patient including for example, blood pressure, blood glucose level, pulse rate, blood coagulation data, weight of the patient, respiratory data, etc. Each remote apparatus 102 of the system 100 may be coupled to one or more sensors 215-221 depending upon the patient's needs. For example, a diabetic patient may need to provide blood glucose level readings to his/her doctor regularly and hence a blood glucose meter may be coupled to his/her remote apparatus 102.

The vital sign data that are measured may be then forwarded to the remote server 105 for healthcare providers' access. The healthcare provider 106 may access the individual's data through their own computers or desktop systems. The remote server 105 may include a patient dialogue and vital signs data module 111 for storing these vital signs along with patient's profile. The patient dialogue and vital signs data module 111 may also store the content of the rule script and message texts that are communicated between healthcare providers and the patients. The patients' profiles may provide help to the healthcare providers 106 in differentiating each patient and providing customized healthcare programs according to his/her medical needs and preferences.

Figure 3:
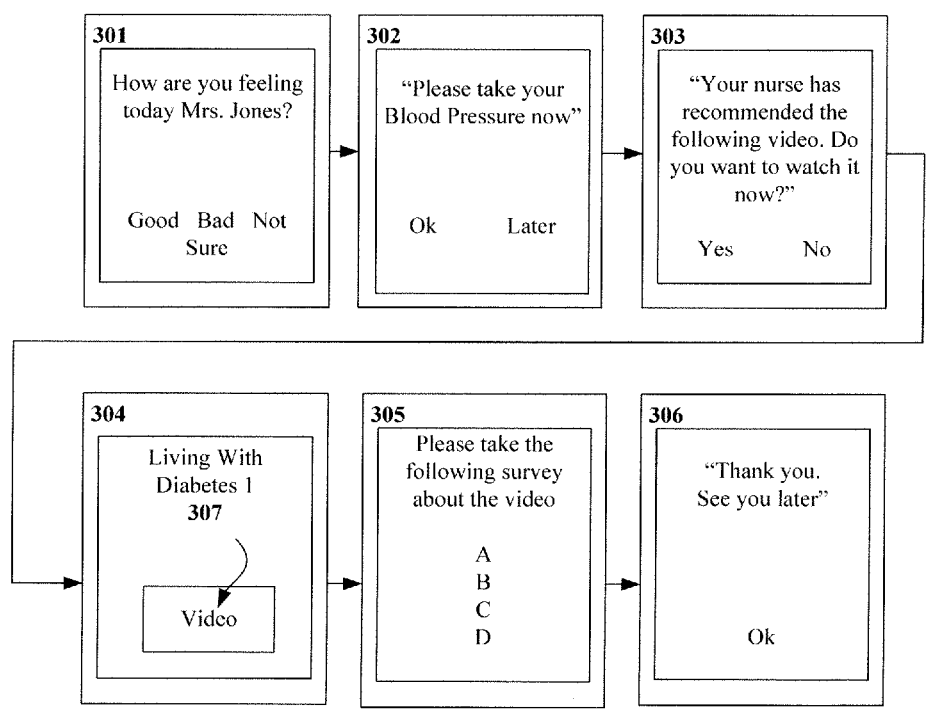
FIG. 3 illustrates an example of a rule script that may be executed on the remote apparatus of FIG. 2 according to an embodiment herein.

Depending upon different medical needs and preferences of the patients, different rule scripts may be generated within the remote server 105. A script generator and response analysis module 110 may be provided in the remote server 105 to generate the rule script in the form of survey questions having a plurality of response choices. The survey questions may be personalized and authored by the healthcare providers 106 through remote server access. The script generator and response analysis module 110 may also allow the healthcare providers 106 to analyze the responses received against the survey questions from different patients or individuals. An example of such a rule script in the form of survey queries having plurality of response choices is shown in FIG. 3. As previously described, the responses received by the remote server 105 also include the information on whether the patient has viewed the video content and whether the patient has comprehended the content. This information may also be sent to the remote server 105 for report generation. The healthcare providers 106 may then access the script generator and response analysis module 110 to receive the patient report for analysis and treatment.

Also, the remote server 105 may include a program schedule and information module 112 for maintaining the program schedules of the video programs that may be received by the remote apparatus 102 from the satellite broadcast stream 101. The satellite broadcast stream 101 may receive the video program data from the video program sources 104 and broadcast the data to each remote apparatus 102 located at various locations within the system 100. The video program data may include different health-related video programs and patient education contents. The video source 104 may have a plurality of channels 113 such as channel 1 114a, channel 2 114b channel 3 114c, and the database 109 for storing schedules of the video program to be delivered to the remote apparatuses 102. The different channels 114a, 114b, 114c may be used to deliver different video programs to the broadcast stream 101. As previously described, the remote apparatuses 102 may be coupled to a television processor 107 having a digital video recorder 108 for receiving the video broadcast data and recording the selected video programs as per the need and preferences of the individuals. As per various embodiments, the remote apparatus 102 may be programmed to instruct the digital video recorder 108 to select appropriate video programs from the video content being received on the television processor 107. The selected video content may be automatically recorded by the digital video recorder 108 on the hard drive 208 (of FIG. 2) of the remote apparatus 102. The program schedule and information module 112 may also maintain description of the video content being broadcast along with the meta-tags to determine the appropriateness of the content. The appropriateness of a video content for an individual may be determined on the basis of the his/her health condition and requirements as well as the responses made by the individual's or patients to the survey script. The program schedule and information module 112 may search program schedule information and determine appropriate educational content and the respective broadcast times. The remote apparatus 102 may then instruct the digital video recorder 108 to record appropriate content as determined by the searched program.

The information on video programs being viewed by the patients along with responses to the educational surveys related to those viewed video programs may also be sent to the remote server 105 for analysis. The remote apparatus 102 collects data from the patient including the video programs that are viewed by the patient. The healthcare provider 106 views patient monitoring data and responses to surveys related to the videos that are viewed by the patient. The healthcare providers 106 may also be allowed to look into the video program schedule 109 to search for appropriate video content available and send a message to the patient device (i.e., remote apparatus 102) indicating that video content should be recorded. For example, if a video content provides physical exercising tips for diabetics, then patients having diabetes may be suggested through message texts to record that video content. Alternatively, the remote apparatuses 102 owned by these patients may be sent instructions to automatically download or record the required video content. The recorded video content may be viewed by the patients or individuals. Each individual or patient may then be queried by the healthcare providers 106 to determine if they have comprehended the health-related content completely. This determination can occur through follow-up questioning of the patients. This enables the healthcare providers 106 to educate their patients' about their health and monitor their health condition easily.

Figure 2:
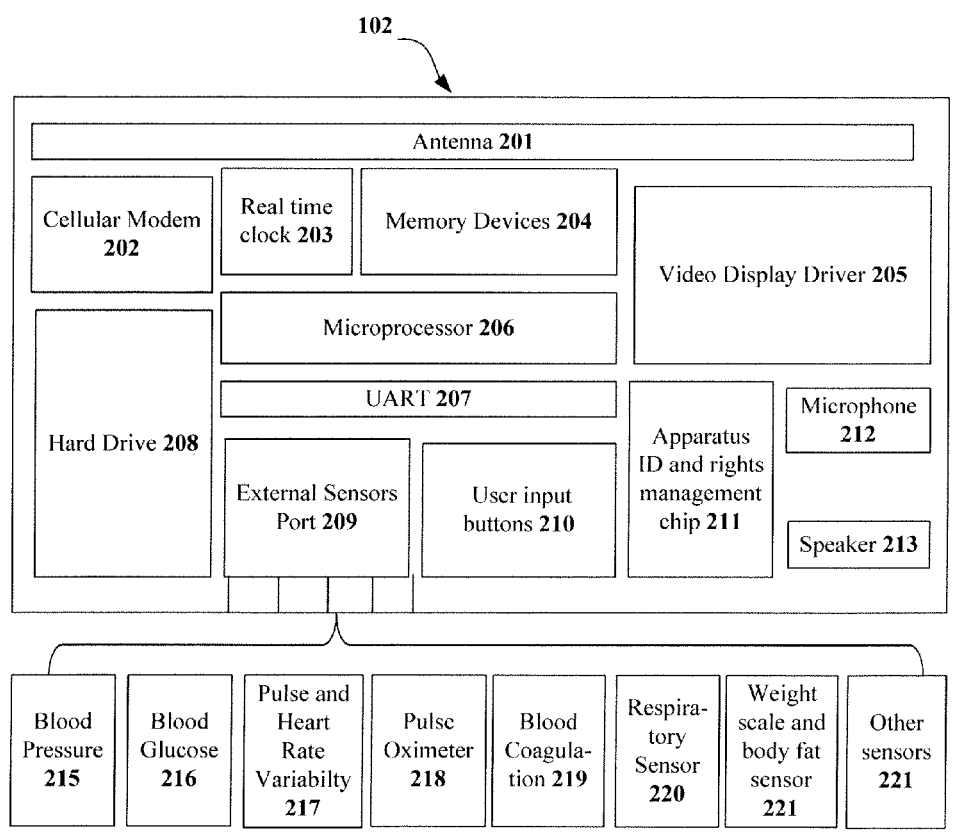
FIG. 2 illustrates a remote apparatus according to an embodiment herein.

FIG. 2 illustrates the remote apparatus 102 (of FIG. 1). The remote apparatus 102 may be embodied as a programmable device capable of collecting various vital sign data and being remotely reprogrammed based on broadcast or cable delivered data and patient's response to the survey questions received. In an embodiment herein, an antenna 201 may be used to receive the broadcast data from the satellite broadcast stream 101 (of FIG. 1). In another embodiment, a cellular modem 202 may be provided for receiving the cable delivered data. A microprocessor 206 may be provided in the remote apparatus 102 and may be configured to execute the rule script (of FIG. 3) sent by the remote server 105 (of FIG. 1). Each apparatus 102 may be provided a unique identification number and the unique identification number along with the patient's profile may be stored in an apparatus ID and rights management chip 211. This enables the remote server 105 (of FIG. 1) to uniquely identify the remote apparatus 102 and accordingly send the appropriate rule script or survey questions.

Memory devices 204 (such as read-only memory (ROM) and random access memory (RAM)) may be provided in the apparatus 102 in association with the microprocessor 206 to store various data and information used by the microprocessor 206. The microprocessor 206 may also produce instructions for the digital video recorder 108 (of FIG. 1) to record the appropriate video program being received. Thus, the remote apparatus 102 may be programmed to record health videos that are appropriate for the patient. The video programs may be recorded in the hard drive 208 provided within the apparatus 102. A video display driver 205 may be provided to allow the patient to view the video programs. The information on the video program viewed and comprehended by the patient may be transmitted along with the vital sign data to the remote server 105 (of FIG. 1) by a transmitter 207. In one embodiment herein, the transmitter 207 may be embodied as a Universal Asynchronous Receiver/Transmitter (UART) 207. An external sensors port 209 may be provided in the apparatus 102 to couple a plurality of health sensors such as blood pressure sensor 215, blood glucose level sensor 216, pulse and heart rate variability sensor 217, pulse oximeter 218, blood coagulation sensor 219, respiratory sensor 220, weight scale and body fat sensor 221, or any other sensor 222.

The microprocessor 206 may also be associated with a real-time clock 203 for indicating the current date and time to the microprocessor 206. The microprocessor 206 processes the data received from the various sensors and the remote server 105 (of FIG. 1). The remote apparatus 102 may also be capable of displaying the rule script through the video display driver 205 or audibly indicating the rule script through a speaker 213. Patients or individuals may be allowed to enter a response to the survey through user input buttons 210 or an audible response by using a microphone 212.

FIG. 3 illustrates an exemplary sequence of a rule script that may be executed on the remote apparatus 102 (of FIGS. 1 and 2) according to an embodiment herein. The rule script in the form of survey questions may be displayed by using the video display driver 205 (of FIG. 2). As shown in FIG. 3, the rule script may include survey questions 301-303 such as 'How are you feeling today Mr. Jones?' 301 and a plurality of response options for each question 301-303. The multiple response options may include for example "Good, Bad, Not Sure" as shown in box 301. The patient may then be asked to take his/her blood pressure through a message 302 saying "Please take your Blood Pressure now" along with the response options as "OK" or "Later" as shown in box 302.

Thereafter, the patient may be asked to watch a particular video by displaying a message 303 "Your nurse has recommended the following video. Do you want to watch it now?" along with the response choices as "Yes or No" as shown in box 303. If the patient is ready to view the video then he/she may be shown an appropriate video for example a video 307 on "Living With Diabetes 1" as shown in box 304. In case the patient is not ready to view the video, then the remote apparatus 102 (of FIG. 1) may be instructed by the remote server 105 (of FIG. 1) to record the video on "Living With Diabetes 1" so that the user may be able to view it later.

In the embodiments herein, the patients may also be surveyed to determine whether he/she has comprehended the video 307 of "Living With Diabetes 1" as shown in box 304. Hence, the patient may be asked to respond to a survey on the video 307 viewed by displaying a message 305 "Please take the following survey about the video" along with the survey items "A, B, C, and D" shown in box 305. The last box 306 shows a thank you message for the patient after the completion of the survey.

Figure 4:
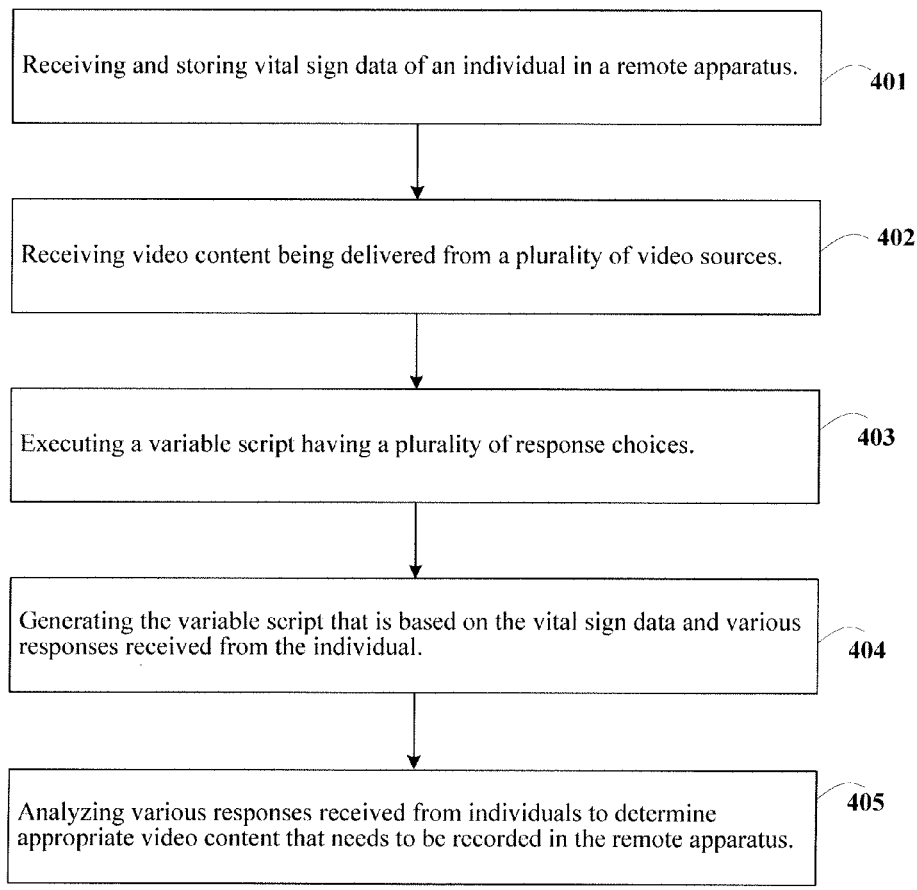
FIG. 4 is a flowchart illustrating a method of health monitoring and imparting health education to individuals according to an embodiment herein.

In the embodiments herein, a method of health monitoring and imparting health education to individuals is shown in FIG. 4 (with respect to FIGS. 1 through 3). The method allows an automated process of health monitoring and health education to various individuals located at different locations. Utilization of appropriate health-related video content for imparting sound knowledge of diseases and healthcare to the individuals is made possible.

The method may comprise the steps of receiving and storing (401) vital sign data of an individual in a remote apparatus 102. The vital sign data may be stored along with a patient's profile and his/her health condition. The health condition of the individual may be collected through various health sensors 215-221 coupled to the remote apparatus 102. The next step involves receiving (402) video content being delivered from a plurality of video sources 104. As per the schedule set for the video programs, the video sources 104 may send a plurality of video program data to the remote apparatus 102 via the satellite broadcast stream 101.

The next step includes executing (403) a rule script having a plurality of response choices, wherein the rule script may be in the form of survey questions 301-303 having a plurality of response choices. The rule script may be generated (404) in a remote server 105 and authored by healthcare providers 106. The remote apparatus 102 may have a user interface 210, 212 enabling the patient to enter the response(s) of the queries 301-306 received.

The various responses received from individuals may be then analyzed (405) by the healthcare providers through remote server access to determine the health condition of the patient and accordingly suggest the patient to view appropriate video content. The remote server 105 may be configured to send a signal to the remote apparatus 102 indicating that the appropriate video content should be recorded.

Thus, the existing video programs and health-related educational content that are available are selected to be viewed by patients and individuals at their end for imparting health education and awareness. Selection of video content is accomplished in an intelligent way by knowing the schedule of the content stream, knowing the patient profile, and assigning a set of rules to the patient's remote apparatus 102. Furthermore, patients are encouraged to view the selected video content by automatically programming the patient's remote apparatus 102 and recording the appropriate content in their respective remote apparatus 102.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A health digital video recording system for remote health management and monitoring, said system comprising:
   a remote server;
   at least one programmable remote apparatus that collects user health information and vital signs using a plurality of sensors and conveys the information and vital signs to a healthcare provider computer through said remote server;

a user interface connected to said at least one programmable remote apparatus, wherein said user interface is accessible by a user;

a television (TV) processor operatively connected to said at least one programmable remote apparatus, said TV processor comprising a digital video recorder, wherein said at least one programmable remote apparatus is programmed to automatically select and record health-related video content being received by said TV processor from a satellite broadcast stream;

a video program source that receives said satellite broadcast stream and is operatively connected to said remote server, wherein said video program source is a separately configured from said remote server;

a patient dialogue and vital signs data module in said remote server that stores said vital signs and a user profile of said user, wherein said patient dialogue and vital signs data module stores content of a rule script generated by said remote server and message texts that are communicated between said healthcare provider computer and said user interface;

a script generator and response analysis module in said remote server that generates said rule script comprising survey questions having a plurality of response choices; and a program schedule and information module in said remote server that maintains program schedules of video programs that are received by said at least one programmable remote apparatus from said satellite broadcast stream, wherein said video program source comprises a video program schedule database, wherein said satellite broadcast stream continuously broadcasts a plurality of video broadcast data according to said video program schedule database, wherein said remote server reads information from said video program schedule database and selects health-related video content from said satellite broadcast stream that is most relevant to a health condition of said user, wherein said health-related video content is integrated with a health management program of said user that enables said user to view, through said user interface, video content appropriate for a current health status of said user, wherein said remote server generates a report indicating whether said user has viewed and comprehended said video content, and wherein said healthcare provider computer accesses said report from said remote server and generates analysis and treatment information for said user.

2. The system of claim 1, wherein said remote server comprises exactly one remote server, and wherein said healthcare provider computer uses said user profile to differentiate amongst different users and provides customized healthcare programs according to medical needs and preferences of a particular user.

3. The system of claim 2, wherein different rule scripts are generated within said remote server based upon different medical needs and preferences of different users.

4. The system of claim 1, wherein said survey questions are personalized and authored by said healthcare provider computer through said remote server.

5. The system of claim 1, wherein said script generator and response analysis module allows said healthcare provider computer to analyze responses received against said survey questions from different users.

6. The system of claim 1, wherein said satellite broadcast stream receives video program data from said video program source and broadcasts the data to each remote apparatus located at various locations within said system.

7. The system of claim 1, wherein said video program source comprises a plurality of channels and said video program schedule database that store schedules of a video program to be delivered to said remote apparatus, and wherein said plurality of channels delivers different video programs to said satellite broadcast stream.

8. The system of claim 1, wherein said digital video recorder receives video broadcast data and records selected video programs according to needs and preferences of said user.

9. The system of claim 1, wherein said at least one programmable remote apparatus is programmed to instruct said digital video recorder to select appropriate video programs from the video content being received on said TV processor, and wherein selected video content is automatically recorded by said digital video recorder on a hard drive of said at least one programmable remote apparatus.

10. The system of claim 9, wherein said at least one programmable remote apparatus comprises a unique identification number.

11. The system of claim 10, wherein said unique identification number enables said remote server to uniquely identify said at least one programmable remote apparatus and send an appropriate rule script or survey question.

12. The system of claim 10, wherein said at least one programmable remote apparatus comprises:
   means for receiving broadcast data from satellite broadcast stream;
   a microprocessor that executes said rule script sent by said remote server;
   an apparatus ID and rights management chip that stores said unique identification number and said user profile;
   a real-time clock operatively connected to said microprocessor;
   a speaker that audibly indicates said rule script;
   means for allowing said user to provide a response to said survey questions; and
   at least one memory device that stores data used by said microprocessor.

13. The system of claim 12, wherein said microprocessor produces instructions for said digital video recorder to record said video programs, and wherein said microprocessor processes data received from said plurality of sensors and said remote server.

14. The system of claim 13, wherein said at least one programmable remote apparatus further comprises:
   a video display driver that allows said user to view said video programs, and allows said rule script to be displayed on said user interface;
   a transmitter that transmits information on the video programs viewed and comprehended by said user, and vital signs data to said remote server; and
   an external sensors port that couples to said plurality of sensors,
   wherein said hard drive stores said video programs.

15. The system of claim 14, wherein said transmitter comprises a Universal Asynchronous Receiver/Transmitter (UART).

16. The system of claim 1, wherein said program schedule and information module maintains a description of the video content being broadcast along with associated meta-tags to determine an appropriateness of said video content, and wherein said appropriateness of said video content for a user is determined by a health condition and requirements of said user as well as responses made by said user to a survey script.

17. The system of claim 1, wherein said program schedule and information module searches program schedule information and determines appropriate educational content and respective broadcast times of the video content, and wherein said at least one programmable remote apparatus instructs said digital video recorder to record appropriate content as determined by a searched program.

18. The system of claim 1, wherein said remote server analyzes the information on video programs being viewed by said user along with responses to said survey questions related to the viewed video programs.

19. The system of claim 1, wherein said healthcare provider computer accesses user monitoring data received from said at least one programmable remote apparatus through said plurality of sensors, and responses to said survey questions related to the video content that is viewed by said user.

20. The system of claim 1, wherein said healthcare provider computer accesses said program schedules to search for appropriate video content available for said user to view and transmits a message to said at least one programmable remote apparatus indicating that said video content should be recorded.

21. The system of claim 1, wherein said at least one programmable remote apparatus receives instructions to automatically download or record said video content appropriate for a current health status of said user.

22. The system of claim 1, wherein said healthcare provider computer sends a query to said user accessible through said user interface to determine if said user has comprehended said video content completely.

23. The system of claim 22, wherein the determination of whether said user has comprehended said video content completely comprises said healthcare provider computer sending follow-up questions to said user accessible through said user interface.

24. The system of claim 1, wherein said at least one programmable remote apparatus is remotely reprogrammable based on broadcast or cable delivered data and responses from said user to said survey questions received through said user interface.

25. The system of claim 1, wherein said plurality of sensors comprise a blood pressure sensor, a blood glucose level sensor, a pulse and heart rate variability sensor, a pulse oximeter sensor, a blood coagulation sensor, a respiratory sensor, and a weight scale and body fat sensor.

* * * * *